US012029433B2

(12) United States Patent
Zhou et al.

(10) Patent No.: US 12,029,433 B2
(45) Date of Patent: Jul. 9, 2024

(54) MEDICAL APPARATUS

(71) Applicant: Suzhou Intocare Medical Technology Co., Ltd, Jiangsu (CN)

(72) Inventors: Bingchao Zhou, Jiangsu (CN); Hui Zhang, Jiangsu (CN); Yunfeng Du, Jiangsu (CN); Dianchen Liu, Jiangsu (CN)

(73) Assignee: INTOCARE MEDICAL TECHNOLOGY (SUZHOU) CO., LTD, Jiangsu (CN)

( * ) Notice: Subject to any disclaimer, the term of this patent is extended or adjusted under 35 U.S.C. 154(b) by 759 days.

(21) Appl. No.: 17/273,348

(22) PCT Filed: Nov. 13, 2019

(86) PCT No.: PCT/CN2019/117964
§ 371 (c)(1),
(2) Date: Mar. 4, 2021

(87) PCT Pub. No.: WO2020/108305
PCT Pub. Date: Jun. 4, 2020

(65) Prior Publication Data
US 2021/0315583 A1 Oct. 14, 2021

(30) Foreign Application Priority Data
Nov. 30, 2018 (CN) .......................... 201811449367.6

(51) Int. Cl.
A61B 17/128 (2006.01)
A61B 17/00 (2006.01)
(Continued)

(52) U.S. Cl.
CPC .. A61B 17/128 (2013.01); A61B 2017/00398 (2013.01); A61B 2017/00407 (2013.01);
(Continued)

(58) Field of Classification Search
CPC ................... A61B 17/128; A61B 2017/00407
See application file for complete search history.

(56) References Cited

U.S. PATENT DOCUMENTS 5,843,097 A 12/1998 Mayenberger et al.
6,059,799 A 5/2000 Aranyi et al.
(Continued)

FOREIGN PATENT DOCUMENTS

CA 3009420 A1 7/2017
CN 1994237 A 7/2007
(Continued)

OTHER PUBLICATIONS

EP Office Action dated Sep. 17, 2021 in EP application No. 19891147.1-1122 / 3834750.
(Continued)

Primary Examiner — Kathleen S Holwerda
Assistant Examiner — Jonathan A Hollm
(74) Attorney, Agent, or Firm — McClure, Qualey & Rodack, LLP

(57) ABSTRACT

A medical apparatus, including a clamp, a work head and a handle; the work head includes a casing, a firing forcing member, a firing rod, a receiving cavity, and a clip-cartridge assembly; an inner cavity communicating with the receiving cavity is formed in the casing; a positioning block is arranged in the inner cavity; the firing forcing member includes a toggle piece and a movable member, the toggle piece having a first connecting part, a second connecting part, and a third connecting part; in condition that the positioning block moves forwards, the toggle piece rotates towards the clamp through the first connecting part to drive the firing rod to control the clamp to open; and in condition that the positioning block moves backwards, the toggle
(Continued)

piece rotates towards the handle through the first connecting part to drive the firing rod to control the clamp to close.

12 Claims, 4 Drawing Sheets

(51) Int. Cl.
    *A61B 17/12*     (2006.01)
    *A61B 90/00*     (2016.01)

(52) U.S. Cl.
    CPC . *A61B 2017/12004* (2013.01); *A61B 17/1285* (2013.01); *A61B 2090/035* (2016.02)

(56) References Cited

U.S. PATENT DOCUMENTS

| | | | |
|---|---|---|---|
| 6,911,033 | B2 | 6/2005 | de Guillebon et al. |
| 7,976,552 | B2 | 7/2011 | Suzuki |
| 8,523,882 | B2 | 9/2013 | Huitema et al. |
| 10,307,166 | B2 | 6/2019 | Willett et al. |
| 10,932,793 | B2 | 3/2021 | Yi et al. |
| 11,464,519 | B2 * | 10/2022 | Zhou ................. A61B 17/1285 |
| 2010/0057102 | A1 | 3/2010 | Sorrentino et al. |
| 2014/0005695 | A1 * | 1/2014 | Shelton, IV ........... A61B 34/30 |
| | | | 606/143 |
| 2014/0324074 | A1 | 10/2014 | Crainich et al. |
| 2018/0116673 | A1 | 5/2018 | Baril et al. |

FOREIGN PATENT DOCUMENTS

| | | |
|---|---|---|
| CN | 101507646 A | 8/2009 |
| CN | 202223293 U | 5/2012 |
| CN | 103181810 A | 7/2013 |
| CN | 103356267 A | 10/2013 |
| CN | 104039248 A | 9/2014 |
| CN | 204336987 U | 5/2015 |
| CN | 106466197 A | 3/2017 |
| CN | 107205748 A | 9/2017 |
| CN | 206867246 U | 1/2018 |
| CN | 107961050 A | 4/2018 |
| CN | 108135602 A | 6/2018 |
| CN | 108209999 A | 6/2018 |
| CN | 108472044 A | 8/2018 |
| WO | 2017120734 A1 | 7/2017 |
| WO | WO-2017120734 A1 * | 7/2017 ......... A61B 17/1285 |

OTHER PUBLICATIONS

Non-Final Office Action issued in U.S. Appl. No. 17/273,330, filed Mar. 4, 2021, mailed Jan. 31, 2024.
EP Search Report dated Sep. 22, 2021 in EP application No. 19891047.3-1122/3834749.
EP Search Report dated Aug. 25, 2021 in EP application No. 19890383.3-1122/3834747.
International Search Report issued Feb. 7, 2020 in application PCT/CN2019/117873.
International Search Report issued Feb. 14, 2020 in application PCT/CN2019/117905.
English translation of International Search Report issued Feb. 7, 2020 in application PCT/CN2019/117873.
English translation of International Search Report issued Feb. 14, 2020 in application PCT/CN2019/117905.

* cited by examiner

MEDICAL APPARATUS

CROSS REFERENCE TO RELATED APPLICATION

This application claims the priority of Chinese Patent Application No. 201811449367.6 filed on Nov. 30, 2018, the entire contents of which are hereby incorporated by reference.

TECHNICAL FIELD

The present disclosure relates to a medical apparatus, belonging to the technical field of medical apparatus.

BACKGROUND

In order to fully expose the surgical visual field during the surgical procedure, it is necessary to ligate the blood vessels around target tissue to arrest bleeding. Hemostasis has become one of the basic surgical operations. Surgical operations in any part of the human body involve bleeding and hemostasis, basically without exception. Generally, a clip applicator for ligation clips is available for performing hemostasis. However, a firing rod of current clip applicator is connected to a driving device. For example, a clamp is in an open state first. Then, a clip-cartridge assembly is driven to feed clips. Finally, the firing rod drives the clamp to close while the clip-cartridge assembly retreats. Such an operation process is complicated and time consuming, which prolongs operation time and reduces operation efficiency.

SUMMARY

The purpose of the present disclosure is to provide a medical apparatus, which allows a firing rod, a clamp and a clip-cartridge assembly to move simultaneously, so as to reduce operation time and increase operation efficiency.

In order to achieve the above-mentioned purpose, the present disclosure provides the following technical solutions: a medical apparatus, comprising: a clamp, a work head and a handle, the work head is connected to the clamp and the handle; the work head comprises a casing, a firing forcing member arranged in the casing, a firing rod connected to the firing forcing member, a receiving cavity arranged at a side of the firing rod, and a clip-cartridge assembly, the clip-cartridge assembly being arranged in the receiving cavity and configured for delivering ligation clips to the clamp. The firing rod is connected to the firing forcing member and the clamp respectively, and the firing forcing member drives the firing rod to move so as to open or close the clamp. An inner cavity communicating with the receiving cavity is formed in the casing, and a positioning block is arranged in the inner cavity. The firing forcing member comprises a toggle piece and a movable member, the toggle piece having a first connecting part, a second connecting part, and a third connecting part, the first connecting part being axially connected to the casing, the second connecting part being connected to the connecting rod, the third connecting part being connected to the movable member, and the positioning block is clamped with the toggle piece. In condition that the positioning block moves forwards, the toggle piece rotates towards the clamp through the first connecting part to drive the firing rod to control the clamp to open; and in condition that the positioning block moves backwards, the toggle piece rotates towards the handle through the first connecting part to drive the firing rod to control the clamp to close.

Further, a guide groove is formed in the casing, and the movable member is disposed in the guide groove.

Further, the movable member comprises a spring and a spring rod, the spring being fixedly arranged in the guide groove and configured for restoring the toggle piece, a spring rod being arranged in the spring; and an end of the spring rod is connected to the toggle piece, and the other end of the spring rod abuts against the spring.

Further, the clip-cartridge assembly comprises the ligation clips, a clip-cartridge slot configured for accommodating the ligation clips, and a clip-pushing piece covering the clip-cartridge slot; the clip-pushing piece is provided with a plurality of ratchet facing towards the clamp, and the ratchet abut against the ligation clips to push the ligation clips to move towards the clamp under driving of a driving rod.

Further, the medical apparatus further comprises a driving rod, the driving rod is arranged on the clip-cartridge assembly to push the clip-pushing piece to move; a clip-pushing forcing member is further arranged on the handle, and the clip-pushing forcing member is connected to the driving rod and drives the driving rod to push the clip-pushing piece to move.

Further, a bending piece is arranged on a side of the clip-cartridge slot, a side of the driving rod facing towards the clip-cartridge slot is provided with a groove, and the groove is configured for receiving the bending piece; a brake member is detachably arranged between the driving rod and the clip-cartridge assembly to limit relative movement between the driving rod and the clip-cartridge slot.

Further, the driving rod is provided with a clamping part, and the positioning block cooperates with the clamping part to restrict the driving rod from moving towards the clamp.

Further, the driving rod comprises a main body part and a bending part bent outwards from a side of the main body part, and the clamping part comprises a latching hook arranged on the bending part and a first bump arranged on the main body part.

Further, the positioning block is arranged between the latching hook and the first bump.

Further, the latching hook is of a slope structure, the slope structure has an inclined plane and a vertical plane connected to the inclined plane, and the vertical plane is clamped with the positioning block.

The present disclosure has the following beneficial effects: by allowing the positioning block to be clamped with the toggle piece, the firing rod is driven to move forwards or backwards so as to control the opening or closing of the clamp, in this way, the firing rod, the clamp, and the clip-cartridge assembly can be operated simultaneously without the need to be operated separately and individually, thereby achieving the purposes of structure simplification, quick firing and efficiency improvement.

The above-mentioned description is only an overview of the technical solution of the present disclosure. In order to understand the technical means of the present disclosure more clearly and implement it according to the contents of the specification, the preferred embodiments of the present disclosure will be described in detail below in conjunction with the accompanying drawings.

DETAILED DESCRIPTION

The specific implementation modes of the present disclosure will be described in further detail with reference to the drawings and embodiments. The following embodiments serve to illustrate the present disclosure, but are not intended to limit the scope of the present disclosure.

Figure 1:
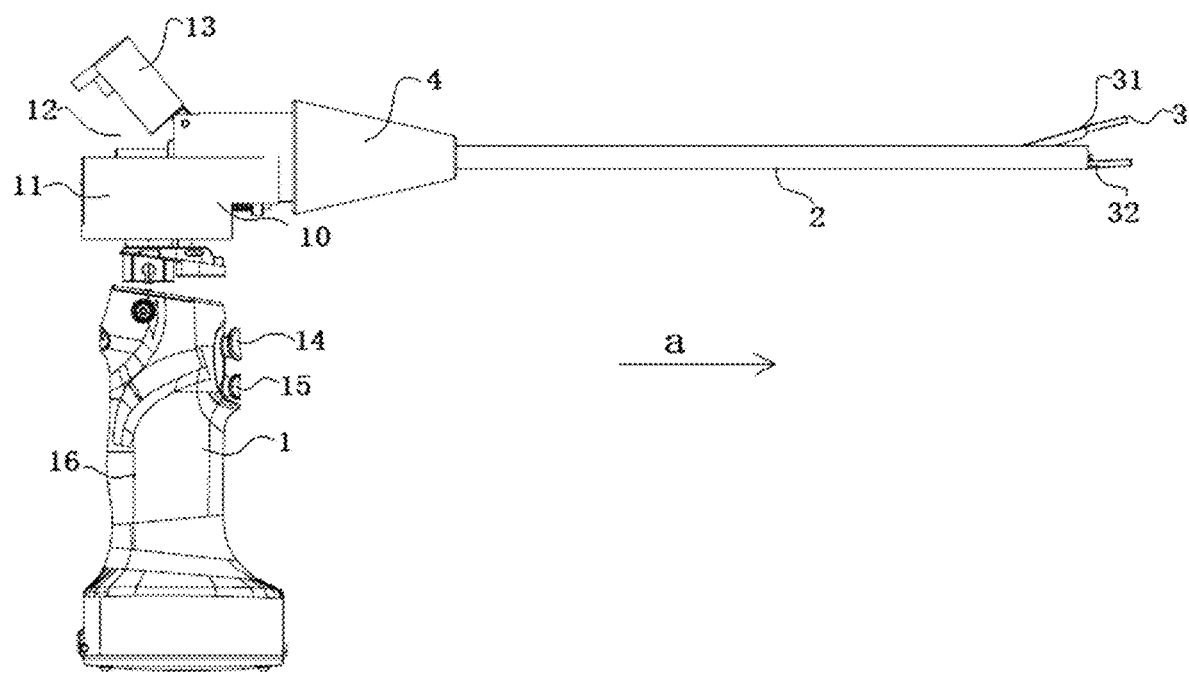
FIG. 1 is a schematic diagram of an overall structure of a medical apparatus provided in the present disclosure.
Figure 2:
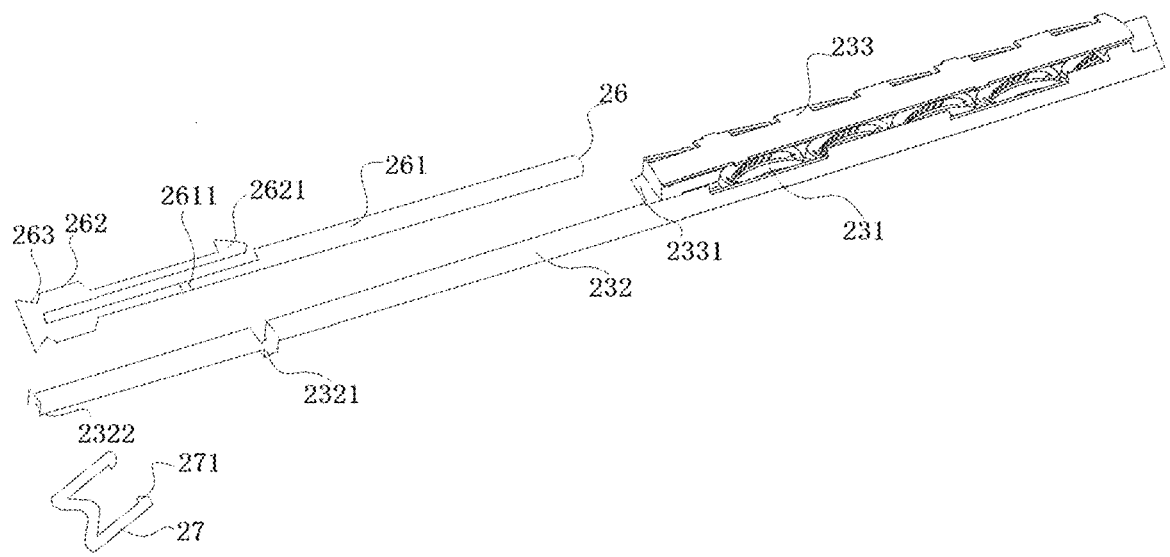
FIG. 2 is a schematically structural diagram of a clip-cartridge assembly in FIG. 1.
Figure 3:
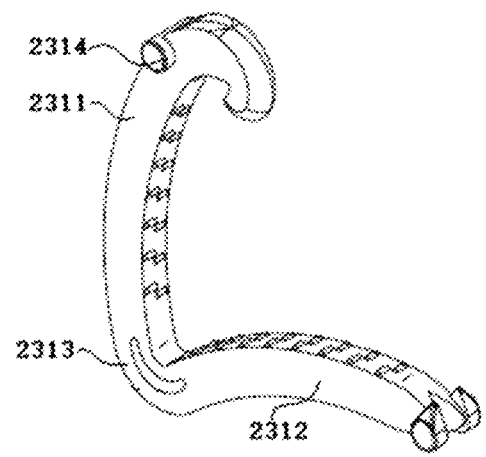
FIG. 3 is a schematically structural diagram of a ligation clip in FIG. 2.
Figure 4:
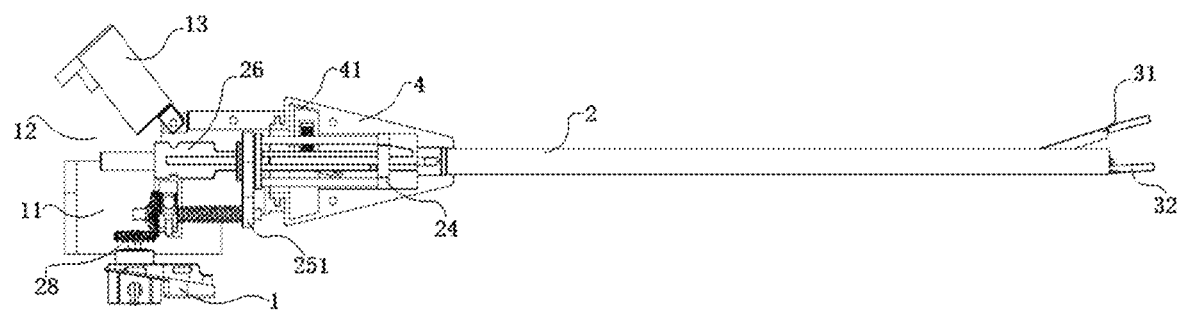
FIG. 4 is a schematically sectional view of a medical apparatus of the present disclosure.
Figure 5:
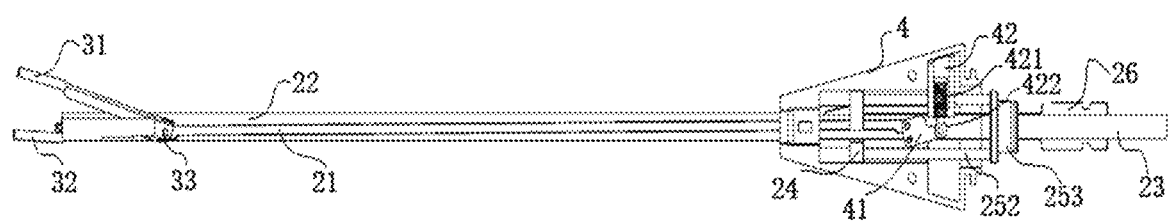
FIG. 5 is another schematically sectional view of a medical apparatus of the present disclosure.
Figure 6:
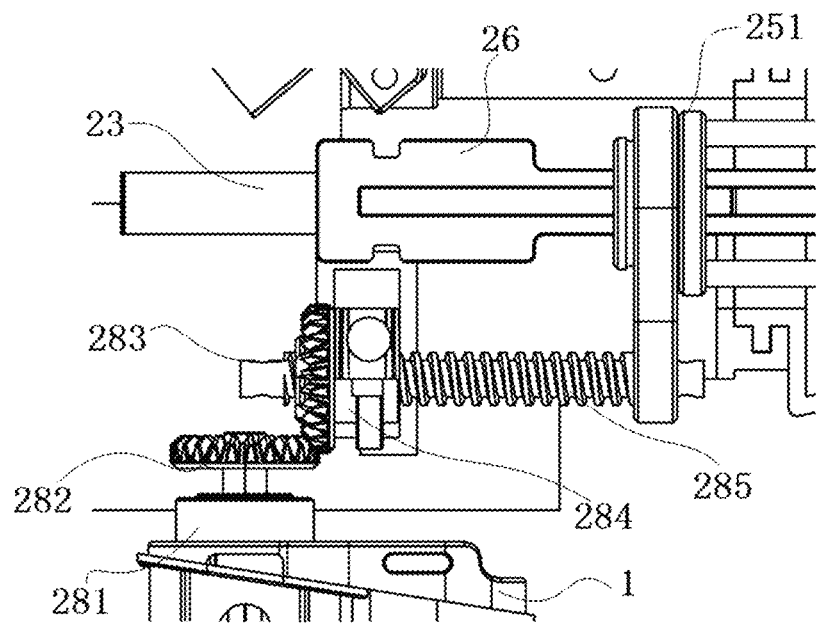
FIG. 6 is a schematically structural diagram of a driving assembly in FIG. 4.
Figure 7:
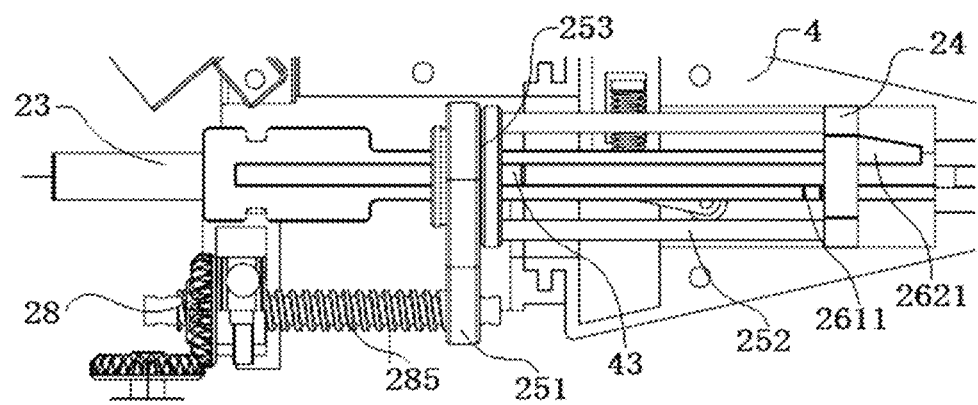
FIG. 7 is a schematically structural diagram of a connecting assembly in FIG. 4.

Referring to FIGS. 1 to 7, a medical apparatus in a preferred embodiment of the present disclosure includes a clamp 3, a work head 2, and a handle 1. The work head 2 is connected to both the clamp 3 and the handle 1. The work head 2 includes a casing 10, a firing forcing member arranged in the casing 10, a firing rod 21 connected to the firing forcing member, a receiving cavity 22 arranged at a side of the firing rod 21, and a clip-cartridge assembly 23 arranged in the receiving cavity 22 and configured for delivering ligation clips 231 to the clamp 3. The firing rod 21 is connected to the firing forcing member and the clamp 3 respectively, and the firing forcing member drives the firing rod 21 to move so as to open or close the clamp 3. An inner cavity 11 communicating with the receiving cavity 22 is formed in the casing 10, and the casing 10 has an opening 12 formed at a side of the inner cavity 11. The clip-cartridge assembly 23 passes through the inner cavity 11 via the opening 12 to be inserted into the receiving cavity 22. A cover 13 connected to the opening 12 is further disposed on the casing 10, and the cover 13 is opened or closed relative to the opening 12.

The clamp 3 includes a movable jaw 31 and a fixed jaw 32, the movable jaw 31 is connected with the fixed jaw 32 by a rotating shaft 33, and the firing rod 21 is connected to the rotating shaft 33. The firing rod 21 moves forward or backward to control the opening or closing of the movable jaw 31 relative to the fixed jaw 32.

The clip-cartridge assembly 23 includes ligation clips 231, a clip-cartridge slot 232 configured for accommodating the ligation clips 231, and a clip-pushing piece 233 covering the clip-cartridge slot 232. The clip-pushing piece 233 is provided with a plurality of ratchet facing towards the clamp 3, and the ratchet abut against the ligation clips 231 to push the ligation clips 231 to move towards the clamp 3 under the driving of a driving rod 26. Each ligation clip 231 includes a first clip arm 2311, a second clip arm 2312, and a connector 2313 configured for connecting the first clip arm 2311 and the second clip arm 2312. Each first clip arm 2311 is further provided with a protrusion 2314. The protrusion allows the ratchet to abut thereon, so as to push the ligation clip 231 to move in the clip-cartridge slot 232 and move towards the clamp 3. The protrusion 2314 is in a shape of cylinder and is arranged at an end, away from the connector 2313, of the first clip arm 2311. The ligation clip 231 is moved in the clip-cartridge slot 232 along a moving direction, and the protrusion 2314 has an inclined surface extending along the moving direction of the ligation clip 231. When the clip-pushing piece 233 feeds the clips, the ratchet abut against the protrusion 2314 to push the ligation clips 231 towards the clamp 3. When the clip-pushing piece 233 retracts, due to that the inclined surface of the protrusion 2314 gradually inclines downwards from the direction of the clamp 3, the ratchet will not interfere with the ligation clips 231 when the ratchet retracts together with the clip-pushing piece 233, and the positions of the ligation clips 231 remain unchanged.

The medical apparatus further includes a driving rod 26 arranged on the clip-cartridge assembly 23; a clip-pushing forcing member is further arranged on the handle 1, and the clip-pushing forcing member is connected to the driving rod 26, so as to drive the driving rod 26 to push the clip-pushing piece 233 to move. The clip-pushing piece 233 is disposed on the clip-cartridge slot 232 and connected to the clip-pushing piece 233. In the embodiment, one end of the clip-pushing piece 233 is provided with a mounting part 2331, and the driving rod is connected to the clip-pushing piece 233 through the mounting part 2331.

A brake member 27 is detachably arranged between the driving rod 26 and the clip-cartridge assembly 23 to limit the relative movement between the driving rod 26 and the clip-cartridge assembly 23. A side of the clip-cartridge slot 232 is provided with a bending piece 2321, and the driving rod 26 has an abutting surface facing away from the clamp 3. The bending piece 2321 abuts on the abutting surface through the brake member 27. The abutting surface is concave to form a groove for receiving the bending piece 2321; alternatively, the abutting surface is a flat surface. The abutting surface is not limited to the above-mentioned embodiments, as long as the abutting surface abuts against the bending piece 2321.

The driving rod 26 is provided with a latching groove 263, and the brake member 27 is provided with a latching block 271 cooperated with the latching groove 263 in a latching mode. In this embodiment, the brake member 27 is M-shaped, and inward bending pieces of the M-shaped brake member 27 are provided with the latching blocks 271. Both sides of one end of the driving rod 26 are provided with the latching grooves 263. The M-shaped brake member 27 fastens the driving rod 26 and the clip-cartridge slot 232 after the latching blocks 271 slide into the latching grooves 263.

The clip-pushing forcing member includes a positioning block 24, a connecting assembly 25 connected to the positioning block 24, and a driving assembly 28 connected to the connecting assembly 25. The driving assembly 28 drives and pushes the connecting assembly 25 so as to drive the positioning block 24 to move.

The positioning block 24 is arranged in the inner cavity 11. The driving rod 26 is provided with a clamping part, and the positioning block 24 cooperates with the clamping part to restrict the driving rod 26 from moving towards the clamp 3. The driving rod 26 includes a main body part 261 and a bending part 262 bent outwards from a side of the main body part 261. The clamping part includes a latching hook 2621 arranged on the bending part 262 and a first bump 2611 arranged on the main body part 261. The positioning block 24 is arranged between the latching hook 2621 and the first bump 2611. The positioning block 24 is provided with a first through hole allowing the clip-cartridge assembly 23 to enter the receiving cavity 22, and the latching hook 2621 passes through the first through hole to abut against the positioning block 24. The latching hook 2621 is of a slope structure. The slope structure has an inclined plane and a vertical plane connected to the inclined plane, and the vertical plane is clamped with the positioning block 24.

Taking the direction of arrow "a" in the figure as the front side, the slope structure inclines upwards from the front side to the rear side. The slope structure passes through the first through hole under the compression of the first through hole, and then elastically recovers to abut against the positioning block 24. In this embodiment, the first bump 2611 and the latching hook 2621 are arranged in different planes to better fix the clip-cartridge assembly 23. Of course, in other embodiments, the first bump 2611 and the latching hook 2621 may also be arranged in the same plane, which is not limited here.

The medical apparatus further includes a limiting member. The limiting member is configured for preventing the clip-cartridge assembly 23 and/or the driving assembly 28 from exceeding the stroke range.

The limiting member includes a first stopper, a second stopper 43 and a second bump 2322. The first stopper is disposed on the casing 10 at a side of the inner cavity 11, and the first stopper abuts against an end of the clip-cartridge assembly 23 to restrict the clip-cartridge assembly 23 from moving towards the handle 1. The second stopper 43 is disposed in the inner cavity 11. The second bump 2322 is disposed on the clip-cartridge slot 232 and clamped with the second stopper 43. The second bump 2322 is located between the first stopper and the second stopper 43. The second stopper 43 is clamped with the second bump 2322 to restrict the movement of the clip-cartridge assembly 23 towards the clamp 3. The arrangement of the first stopper, the second stopper 43 as well as the second bump 2322 forms the first positional limiting protection for the clip-cartridge assembly 23. When an end of the clip-cartridge assembly 23 abuts against the first stopper or the second bump 2322 abuts against the second stopper 43, the medical apparatus stops working.

The limiting member includes a threaded rod 285 arranged on the driving assembly 28. The threaded rod 285 is connected to the clip-cartridge assembly 23 through the connecting assembly 25. The threaded rod 285 is in threaded connection with the connecting assembly 25. The driving assembly 28 drives the threaded rod 285 to push the connecting assembly 25 so as to drive the clip-cartridge assembly 23 to feed clips. When the driving assembly 28 drives the threaded rod 285 beyond the stroke range, the medical apparatus stops working. The driving assembly 28 is disposed in the handle 1. The driving assembly 28 further includes a driving motor 281, a first gear 282 connected to the driving motor 281, a second gear 283 engaged with the first gear 282 along a vertical direction, and a nut 284 connected to the second gear 283. The nut 284 is sleeved with the second gear 283. The driving motor 281 is provided with an output shaft, and the output shaft is sleeved with the first gear 282. The output shaft transmits the speed and torque output from the driving motor 281 to the first gear 282 and the second gear 283, such that the radial rotation is converted into axial rotation. The driving assembly 28 is in threaded connection with the connecting assembly 25 through the threaded rod 285. The limitation on the length of the threaded rod 285 serves as a third positional limiting protection for the medical apparatus.

The limiting member includes an electronic switch arranged on the clip-cartridge assembly 23, and a receiver arranged in the inner cavity 11 and coupled with the electronic switch. The electronic switch cooperates with the receiver to form a second positional limiting protection for the clip-cartridge assembly 23. When the receiver receives a signal from the electronic switch, the medical apparatus stops working. In this embodiment, the limiting member includes two electronic switches, namely, a first electronic switch and a second electronic switch. The first electronic switch and the second electronic switch are arranged on the two sides of the clip-cartridge assembly 23 to prevent the clip-cartridge assembly 23 from exceeding the stroke range. The electronic switches are conventional position switches, which are not described in detail here. The electronic switches may also be arranged on the connecting assembly 25 and/or the positioning block 24, which is determined according to actual application requirements and not specifically limited here.

Depending on the specific situation, the above-mentioned three positional limiting protections may be arbitrarily combined with one another.

The connecting assembly 25 includes a connecting piece 251 and a connecting rod 252. The connecting rod 252 connects the connecting piece 251 and the positioning block 24. The threaded rod 285 is connected to the connecting piece 251. The driving assembly 28 drives the threaded rod 285 to move forwards, so that the connecting piece 251 drives the positioning block 24 to move, thereby driving the clip-cartridge assembly 23 to move towards the clamp 3. The connecting piece 251 is provided with a second through hole and a three through hole. The threaded rod 285 is in threaded connection with the third through hole, and the clip-cartridge assembly 23 passes through the second through hole to enter the receiving cavity 22. Of course, the connecting assembly 25 may further include a connecting sleeve 253, and the connecting sleeve 253 is sleeved with the connecting piece 251. In this case, the connecting rod 252 connects the connecting sleeve 253 and the positioning block 24.

The firing forcing member includes a toggle piece 41 and a movable member 42. The toggle piece 41 has a first connecting part, a second connecting part, and a third connecting part. The first connecting part is axially connected to the casing 10, the second connecting part is connected to the connecting rod 252, and the third connecting part is connected to the movable member 42. The positioning block 24 is clamped with the toggle piece 41. In this embodiment, the first connecting part, the second connecting part and the third connecting part form a shape of triangle, which can better drive the firing rod 21 to move forwards or backwards in a situation that the toggle piece 41 leans forwards or backwards. When the positioning block 24 moves forwards, the toggle piece 41 rotates towards the clamp 3 through the first connecting part, so as to drive the firing rod 21 to open the clamp 3. When the positioning block 24 moves backwards, the toggle piece 41 rotates towards the handle 1 through the first connecting part, so as to drive the firing rod 21 to close the clamp 3. A guide groove is formed in the casing 10, and the movable member 42 is disposed in the guide groove. The movable member 42 includes a spring 421 and a spring rod 422. The spring 421 is fixedly arranged in the guide groove and configured for restoring the toggle piece 41. The spring rod 422 is arranged in the spring 421. One end of the spring rod 422 is connected to the toggle piece 41, and the other end of the spring rod 422 abuts against the spring 421. When the positioning block 24 moves backwards, the toggle piece 41 presses backwards to deform the spring 421. When the positioning block 24 moves forwards, the spring 421 drives the toggle piece 41 to recover by using the elastic force in itself.

Of course, in other embodiments, the firing forcing member may be a firing handle, and the firing handle is directly connected to the firing rod 21 to drive the firing rod 21 to achieve a firing action, which is not limited here.

The medical apparatus further includes a rotating handle 4 configured for connecting the handle 1 with the work head 2. The angle of the clamp 3 can be regulated by adjusting the rotating handle 4, thereby reducing the difficulty of adjusting the angle of the clamp 3 due to angle limitation during operation. In this embodiment, the second stopper 43 and the guide groove are both disposed on the rotating handle 4.

The handle 1 includes a shell 16, a control circuit arranged in the shell 16, a first switch 14 and a second switch 15; the first switch 14 and the second switch 15 are coupled to the control circuit. The first switch 14 is configured for driving the driving rod 26 and the firing rod 21 to move forwards. The second switch 15 is configured for driving the driving rod 26 and the firing rod 21 to move backwards. The driving assembly 28 is coupled to the control circuit. The handle 1 further includes a battery coupled to the control circuit and a display disposed on the handle 1.

A control module for the driving assembly 28, a work-head identification module, a stroke control module for clip-cartridge feeding and firing, a battery detection-control module, a machine working-state indication module, and a data recording-storage module are disposed in the control circuit and are controlled by a single chip processor.

Herein, the control module for the driving assembly 28 is configured for controlling the start and stop of the threaded rod 285. The first switch 14 and the second switch 15 arranged under the handle 1 are isolated from the interior of a host of a clip applicator. The driving assembly 28 is controlled by moving magnets inside the first switch 14 and the second switch 15 close to or away from a Hall switch sealed in the handle 1.

The identification module for work head 2 is configured for transmitting the type data of the work head 2 through a terminal arranged on the receiving cavity 22, and then instructing the control circuit to call corresponding working programs.

The stroke control module for clip-cartridge feeding and firing realizes clip feeding and clip firing actions by means of a signal identification module, an electronic switch position control module and a safety module installed in the work head 2.

The battery detection module in the battery detection-control module has a function for detecting the battery power and monitors the battery power before and during the surgical operation, in order to ensure that the battery power can meet the surgical operation requirements or allow timely battery replacement.

The working-state indication module is configure for displaying the battery power, the connection state of the work head 2, the clip feeding completion state and the firing completion state by using a display.

The working process of the medical apparatus provided by the present disclosure is as follows: when the first switch 14 is pressed, the driving assembly 28 drives the driving rod 26 through the threaded rod 285 to push the clip-pushing piece 233 forwards, until the ligation clips 231 are pushed into the clamp 3. At the same time, the firing rod 21 moves forwards, so that the clamp 3 is in an open state. Then, the second switch 15 is pressed, the driving assembly 28 drives the driving rod 26 through the threaded rod 285 to drive the clip-pushing piece 233 to move backwards, and the firing rod 21 moves backwards at the same time, so that the clamp 3 is closed to ligate the target tissue.

To sum up, by forming the opening 12 in the casing 10, the clip-cartridge assembly 23 can enter or exit the cavity through the opening 12 to deliver the ligation clips 231 to the clamp 3. In this way, the clip-cartridge assembly 23 can be replaceable, and the clamp 3, the work head 2 and the handle 1 can be reused, thereby achieving the purpose of saving costs.

By placing the plurality of ligation clips 231 in the clip-cartridge assembly 23 and delivering the ligation clips to the clamp 3, the problems of inconvenient use and the increased operational risk in existing apparatuses caused by being incapable of successive feeding the ligation clips are solved.

By constructing the plurality of limiting protections, the safety factor of the medical apparatus is relatively much higher, thus the probability of failure due to a single fault is effectively reduced.

By allowing the positioning block 24 to be clamped with the toggle piece 41, the firing rod 21 is driven to move forwards or backwards so as to control the opening or closing of the clamp 3; in this way, the firing rod 21, the clamp 3, and the clip-cartridge assembly 23 can be operated simultaneously without the need to be operated separately and individually, thereby achieving the purposes of structure simplification, quick firing and efficiency improvement.

The technical features of above-mentioned embodiments can be arbitrarily combined with one another. In order to make the description concise, all possible combinations of the technical features in above-mentioned embodiments are not described. However, as long as no contradiction exists in the combinations of these technical features, they should be considered as part of the disclosure in the present disclosure.

The above-mentioned embodiments only represent several exemplary implementation of the present disclosure; although the embodiments are described in a specific and detailed way, but they cannot be understood as limiting the protection scope of the present disclosure. It should be pointed out that, several modifications and improvements can be made for those ordinary skilled in the art without departing from the concept of the present disclosure, the modifications and improvements belong to the protection scope of the present disclosure. Accordingly, the protection scope of the present disclosure shall be defined by the accompanying claims.

The invention claimed is:

1. A medical apparatus, comprising a clamp, a work head and a handle, wherein the work head is connected to the clamp and the handle; the work head comprises a casing, a firing forcing member arranged in the casing, a firing rod connected to the firing forcing member, a receiving cavity arranged at a side of the firing rod, and a clip-cartridge assembly, the clip-cartridge assembly being arranged in the receiving cavity and configured for delivering ligation clips to the clamp; the firing rod is connected to the firing forcing member and the clamp respectively, and the firing forcing member drives the firing rod to move so as to open or close the clamp; an inner cavity communicating with the receiving cavity is formed in the casing; a positioning block is arranged in the inner cavity; the firing forcing member comprises a toggle piece and a movable member, the toggle piece having a first connecting part, a second connecting part, and a third connecting part, the first connecting part being axially connected to the casing, the second connecting part being connected to a connecting rod, the third connecting part being connected to the movable member, and the positioning block is clamped with the toggle piece; in condition that the positioning block moves forwards, the toggle piece rotates towards the clamp through the first connecting part to drive the firing rod to control the clamp to open; and in condition that the positioning block moves backwards, the toggle piece rotates towards the handle through the first connecting part to drive the firing rod to control the clamp to close,
  wherein the medical apparatus further comprises a limiting member, the limiting member is configured for preventing at least one of the clip-cartridge assembly and a driving assembly from exceeding a stroke range;
  wherein the limiting member comprises a threaded rod arranged on the driving assembly, the threaded rod is connected to the clip-cartridge assembly through a connecting piece, and the threaded rod is in threaded connection with the connecting piece; and the driving assembly drives the threaded rod to push the connecting piece so as to drive the clip-cartridge assembly to feed; in condition that the driving assembly drives the threaded rod beyond the stroke range, the medical apparatus stops working.

2. The medical apparatus according to claim 1, wherein a guide groove is formed in the casing, and the movable member is disposed in the guide groove.

3. The medical apparatus according to claim 2, wherein the movable member comprises a spring and a spring rod, the spring being fixedly arranged in the guide groove and configured for restoring the toggle piece, the spring rod being arranged in the spring; and an end of the spring rod is connected to the toggle piece, and the other end of the spring rod abuts against the spring.

4. The medical apparatus according to claim 1, wherein the clip-cartridge assembly comprises the ligation clips, a clip-cartridge slot configured for accommodating the ligation clips, and a clip-pushing piece covering the clip-cartridge slot; the clip-pushing piece is provided with a plurality of ratchets facing towards the clamp, and the ratchets abut against the ligation clips to push the ligation clips to move towards the clamp under driving of a driving rod.

5. The medical apparatus according to claim 4, wherein the medical apparatus further comprises a driving rod, the driving rod is arranged on the clip-cartridge assembly to push the clip-pushing piece to move; a clip-pushing forcing member is further arranged on the handle, and the clip-pushing forcing member is connected to the driving rod and drives the driving rod to push the clip-pushing piece to move.

6. The medical apparatus according to claim 5, wherein a bending piece is arranged on a side of the clip-cartridge slot, a side of the driving rod facing towards the clip-cartridge slot is provided with a groove, and the groove is configured for receiving the bending piece; a brake member is detachably arranged between the driving rod and the clip-cartridge assembly to limit relative movement between the driving rod and the clip-cartridge slot.

7. The medical apparatus according to claim 6, wherein the driving rod is provided with a clamping part, and the positioning block cooperates with the clamping part to restrict the driving rod from moving towards the clamp.

8. The medical apparatus according to claim 7, wherein the driving rod comprises a main body part and a bending part bent outwards from a side of the main body part, and the clamping part comprises a latching hook arranged on the bending part and a first bump arranged on the main body part.

9. The medical apparatus according to claim 8, wherein the positioning block is arranged between the latching hook and the first bump.

10. The medical apparatus according to claim 8, wherein the latching hook is of a slope structure, the slope structure has an inclined plane and a vertical plane connected to the inclined plane, and the vertical plane is clamped with the positioning block.

11. The medical apparatus according to claim 1, wherein the limiting member comprises a first stopper disposed on the casing at a side of the inner cavity, and the first stopper abuts against an end of the clip-cartridge assembly to restrict the clip-cartridge assembly from moving towards the handle.

12. The medical apparatus according to claim 11, wherein the limiting member further comprises a second stopper disposed in the inner cavity and a second bump; the second bump is disposed on the clip-cartridge assembly and clamped with the second stopper; the second bump is located between the first stopper and the second stopper; in condition that an end of the clip-cartridge assembly abuts against the first stopper or the second bump abuts against the second stopper, the medical apparatus stops working.

\* \* \* \* \*